US011255783B2

(12) United States Patent
Fairey et al.

(10) Patent No.: US 11,255,783 B2
(45) Date of Patent: Feb. 22, 2022

(54) SYSTEMS AND PROCESSES FOR EARLY DETECTION OF BIOLOGICAL AMMONIA OXIDATION IN WATER USING FLUOROMETRY

(71) Applicants: BOARD OF TRUSTEES OF THE UNIVERSITY OF ARKANSAS, Little Rock, AR (US); GARVER, LLC, North Little Rock, AR (US); THE UNITED STATES OF AMERICA, AS REPRESENTED BY THE ADMINISTRATOR OF U.S. ENVIRONMENTAL PROTECTION AGENCY, Washington D.C., DC (US)

(72) Inventors: Julian Fairey, Fayetteville, AR (US); Thien Duc Do, Fayetteville, AR (US); Ashley Pifer, Fayetteville, AR (US); David Wahman, Cincinnati, OH (US)

(73) Assignees: BOARD OF TRUSTEE OF THE UNIVERSITY OF ARKANSAS, Little Rock, AR (US); THE UNITED STATES OF AMERICA, AS REPRESENTED BY THE ADMINISTRATOR OF U.S. ENVIRONMENTAL PROTECTION, Washington, DC (US)

( * ) Notice: Subject to any disclaimer, the term of this patent is extended or adjusted under 35 U.S.C. 154(b) by 216 days.

(21) Appl. No.: 16/556,726

(22) Filed: Aug. 30, 2019

(65) Prior Publication Data

US 2020/0072750 A1 Mar. 5, 2020

Related U.S. Application Data

(60) Provisional application No. 62/724,741, filed on Aug. 30, 2018.

(51) Int. Cl.
*G01N 21/64* (2006.01)
*G01N 33/18* (2006.01)
*G01N 21/84* (2006.01)

(52) U.S. Cl.
CPC ......... *G01N 21/64* (2013.01); *G01N 21/6486* (2013.01); *G01N 33/18* (2013.01); *G01N 33/1846* (2013.01); *G01N 2021/6495* (2013.01); *G01N 2021/6497* (2013.01); *G01N 2021/8416* (2013.01); *Y10T 436/175383* (2015.01)

(58) Field of Classification Search
CPC ............... G01N 21/64; G01N 21/6486; G01N 2021/6495; G01N 2021/6497; G01N 2021/8416; G01N 33/18; G01N 33/1846; G01N 33/188; Y10Y 436/17; Y10Y 436/173076; Y10Y 436/175383; Y10Y 436/235; Y10T 436/17; Y10T 436/173076; Y10T 436/175383; Y10T 436/235
USPC ......... 436/39, 106, 110, 113, 146, 164, 172; 422/82.05, 82.08
See application file for complete search history.

(56) References Cited

U.S. PATENT DOCUMENTS

2016/0122201 A1* 5/2016 Gilmore ................ G01N 33/18
 700/271
2017/0284940 A1 10/2017 Butte et al.

FOREIGN PATENT DOCUMENTS

| CN | 104597004 A | 5/2015 |
| CN | 105466893 A | 4/2016 |
| CN | 105866088 A | 8/2016 |
| WO | 01/55717 | * 8/2001 |

OTHER PUBLICATIONS

Lavonen, E.E., et al., "Tracking changes in the optical properties and molecular compostion of dissolved organic matter during drinking water production," Water Research, vol. 85 Nov. 15, 2015, pp. 286-294, United States.
Kirmeyer, Gregory J., et al., "Nitrification Occurrence and Control in Chloraminated Water Systems," American Water Works Association, 1995, pp. 1-258, United States.
Pifer, Ashley D., et al., "Improving on SUVA254 using Fluorescence-PARAFAC analysis and asymmetric flow-field flow fractionation for assessing disinfection byproduct formation and control," Water Research, vol. 46 Jun. 1, 2012, pp. 2927-2936, United States.
Sorenson, J.P.R., et al., "In-situ tryptophan-like fluorescence: A real-time indicator of faecal contamination in drinking water supplies," Water Research, vol. 81, Sep. 15, 2015, pp. 38-46, United Kingdom.
U.S. Environmental Protection Agency, "Detection of Biological Suspensions Using Online Detectors in a Drinking Water Distribution System Simulator," EPA/600/4-10/005/Mar. 2010, pp. 1-15, United States.

(Continued)

*Primary Examiner* — Maureen Wallenhorst
(74) *Attorney, Agent, or Firm* — Crowe & Dunlevy, P.C.

(57) ABSTRACT

This invention relates generally to a system and process for early detection of biological ammonia oxidation in water utilizing a fluorescence-based sensor and process. Various embodiments are configured to read increases in a fluorescence excitation-emission wavelength pair that is responsive to a period of time (days to weeks or even longer) prior to the onset of biological ammonia oxidation, which is considered to be a nitrification event. Fluorescence excitation/emission pairs that have proven to be reliable include a fluorescence excitation wavelength of about 230 nm and an emission wavelength of about 345 nm and an excitation wavelength of 325 and an emission wavelength of 470. The system and process enable drinking water utilities to improve management of its distribution systems and facilitate earlier corrective actions, resulting is less loss of treated water through flushing and other tangible benefits.

25 Claims, 7 Drawing Sheets

(56) References Cited

OTHER PUBLICATIONS

Van den Hoven, et al., "Real-time on-line monitoring of contaminants in water," Awwa Research Foundation, May 16, 2008, pp. 1-26, The Netherlands.

Zhang, Yan, et al., "Nitrification in Drinking Water Systems," Critical Reviews in environmental Science and Technology, 39:153-208, 2009, United States.

Manual of Water Supply Practices M56, Second Edition, Nitrification Prevention and Control in Drinking Water, American Water works, 2013, United States.

USGS Scientific Investigations Report 2013-5001, Sources and Characteristics of Organic Matter in the Clackamas River, Oregon, Related to the Formation of Disinfection By-Products in Treated Drinking Water, pp. 1-92, United States.

Fleming, Kala K., et al., "Nitrification potential curves: a new strategy for nitrification prevention," Journal AWWA, 97-8, Aug. 2005, pp. 90-99, United States.

Hambly, A.C., et al., "Fluorescence monitoring at a recycled water treatment plant and associated dual distribution system—Implications for cross-connection detection," Water Research 44 (2010), pp. 5323-5333, Australia.

\* cited by examiner

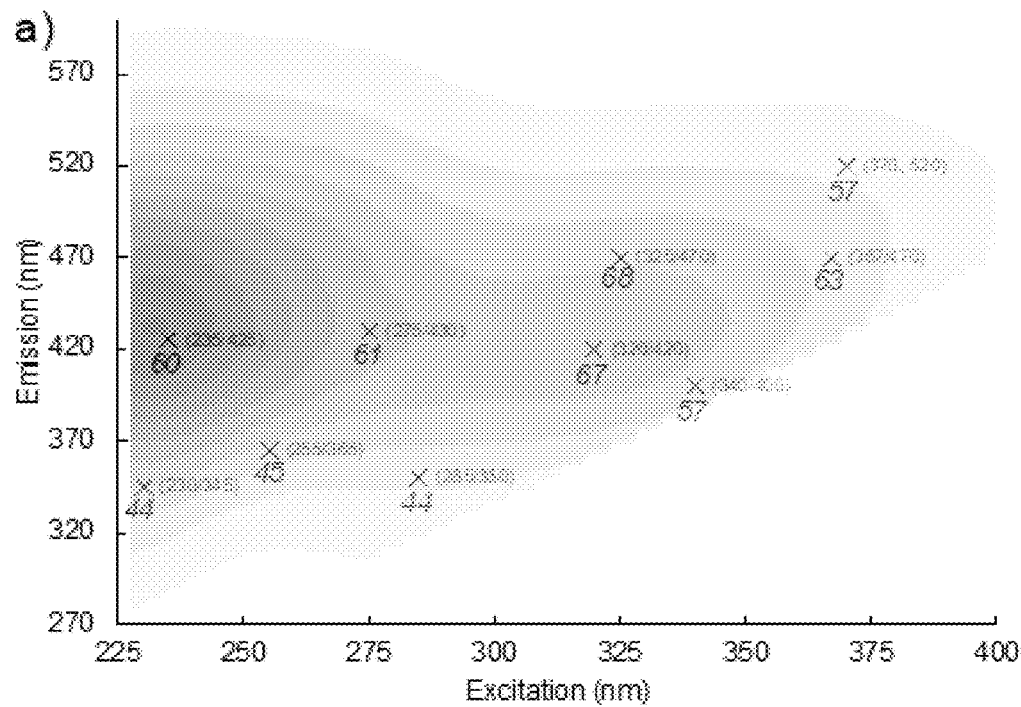
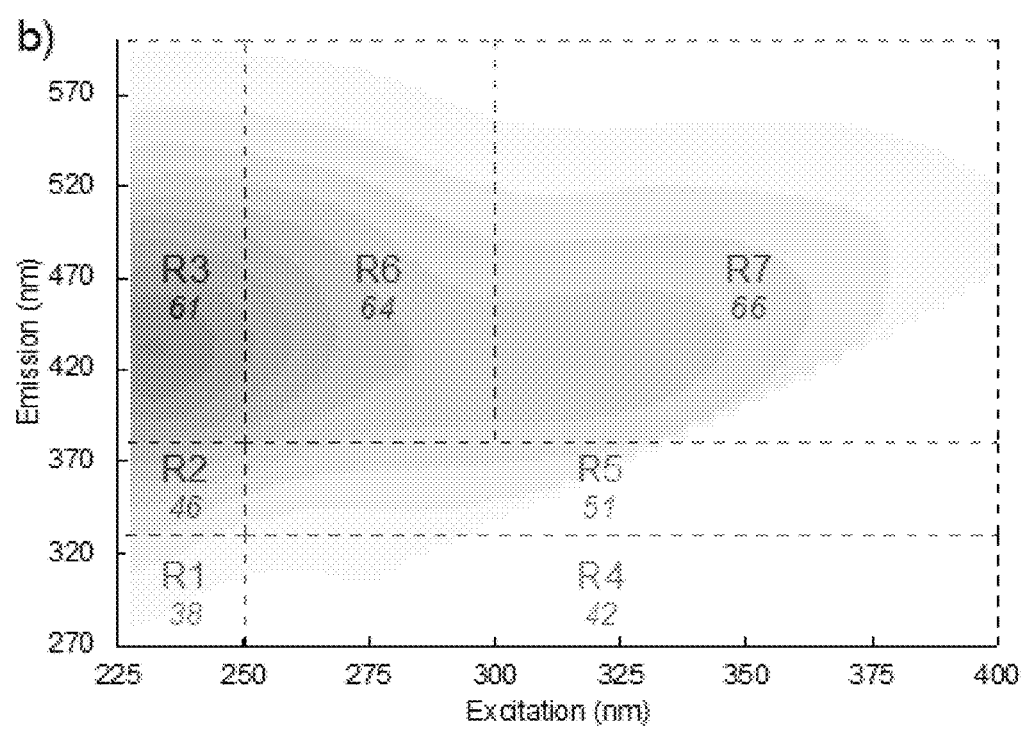
FIG. 5A
FIG. 5B

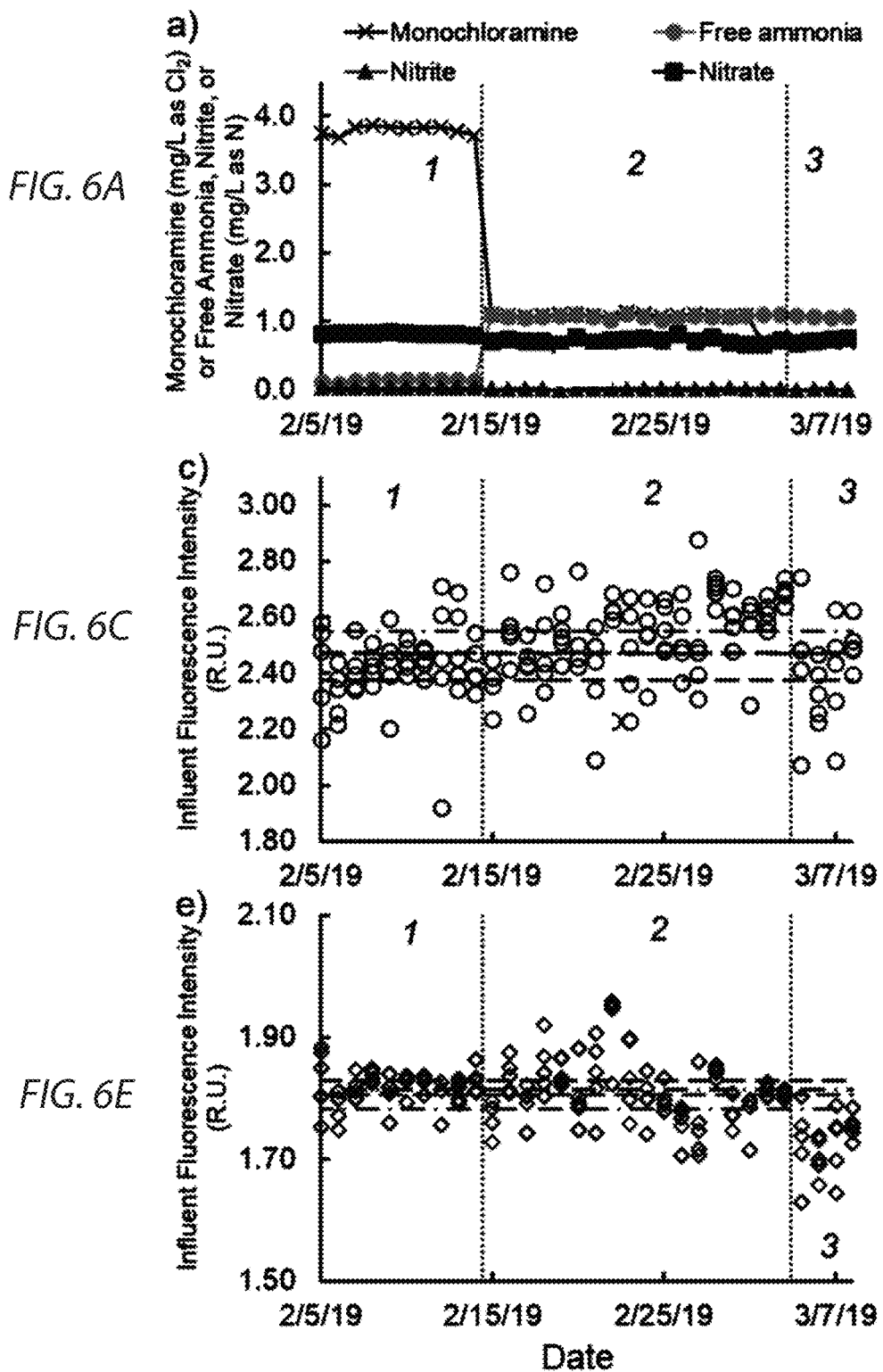

SYSTEMS AND PROCESSES FOR EARLY DETECTION OF BIOLOGICAL AMMONIA OXIDATION IN WATER USING FLUOROMETRY

CROSS REFERENCE TO RELATED APPLICATIONS

The application claims the benefit of and priority to U.S. Provisional Patent Application No. 62/724,741, filed Aug. 30, 2018, and incorporates by reference said provisional application in its entirety.

BACKGROUND OF THE INVENTION

1. Field of the Invention

This invention relates generally to systems and processes for early detection of biological ammonia oxidation in water using fluorometry.

2. Description of the Related Art

Biological ammonia oxidation is a microbial process in which nitrogen compounds are oxidized to nitrite and nitrate. This process is most concerning when it occurs in drinking water distribution systems and can result in disinfectant depletion/loss, nitrite/nitrate formation, dissolved oxygen depletion, reduction in pH and alkalinity, increased microbial presence, etc., the net result of which is a general degradation in drinking water quality. Various potential health impacts have been identified in drinking water that has undergone this process. Water that has experienced significant biological ammonia oxidation requires remedial action, which remedial action might include chemical treatment or flushing the affected distribution system. Flushing of the distribution system can result in losses of billions of gallons of treated water per year for large water utilities. In addition, biological ammonia oxidation can lead to chemical and biological degradation of water quality and can potentially impact compliance with the United States Safe Drinking Water Act.

As such, what is needed is a system and/or process that provides an early warning of biological ammonia oxidation so that remedial action can be taken prior to degradation in water quality. Such a system or process could be very helpful to water utilities that experience biological ammonia oxidation events by alerting them to the problem sooner, and permitting less disruptive and/or costly remedial actions.

It is therefore desirable to provide a system and process for early detection of biological ammonia oxidation in water using fluorometry.

It is further desirable to provide a system and process for early detection of biological ammonia oxidation in water utilizing fluorometry to read changes in one or more fluorescence excitation-emission wavelength pairs or related fluorescence metric(s) that is responsive to a period of time (several days to weeks or even longer) prior to the onset of measurable biological ammonia oxidation, which is considered to be a nitrification event.

It is still further desirable to provide a system and process for early detection of biological ammonia oxidation in water using fluorometry without the use of chemicals and/or sample preparation and processing steps.

Before proceeding to a detailed description of the invention, however, it should be noted and remembered that the description of the invention which follows, together with the accompanying drawings, should not be construed as limiting the invention to the examples (or embodiments) shown and described. This is so because those skilled in the art to which the invention pertains will be able to devise other forms of this invention within the ambit of the appended claims.

SUMMARY OF THE INVENTION

In general, in a first aspect, the invention relates to a system for early detection of biological ammonia oxidation in drinking water. In some embodiments the system includes a fluorescence-based instrument configured to read a fluorescence excitation-emission wavelength pair that is responsive in a period of time prior to an onset of biological ammonia oxidation or a nitrification event. The system could also include electronics and analytical software technology to take fluorescence readings using the fluorescence-based instrument at a fluorescence excitation wavelength of approximately 230 nm and an emission wavelength of approximately 345 nm as an indicator of microbial activity or, as described hereinafter, in some cases a fluorescence excitation wavelength of approximately 325 nm and an emission wavelength of approximately 470 nm could also be used. This will be referred to herein as 230/345 nm or 325/470 nm, respectively. In addition, the fluorescence-based instrument can be a real-time fluorescence-based system in communication with a software to account for water quality derived interferences.

According to another embodiment, in view of the fact that most drinking water that undergoes biological ammonia oxidation tend to have greater total organic carbon (ca. 1-5 mg·L$^{-1}$ as C), a fluorescence wavelength pair at an excitation of approximately 325/470 nm may be preferred for early detection of biological ammonia oxidation. That being stated, the 230/340 nm combination would be useful in all waters and that combination is preferable to 325/470 nm for waters with low total organic carbon (e.g., less than ca. 1 mg·L$^{-1}$ as C).

According to another aspect, the invention relates to a process for early detection of biological ammonia oxidation in drinking water. The process includes obtaining a water sample from a drinking water distribution system, reading signals from a fluorescence-based instrument of a fluorescence excitation-emission wavelength pair in the water sample, and then detecting impending biological ammonia oxidation based on this signal(s). The process can also include facilitating an early remedial action for the drinking water distribution system based on a detected biological ammonia oxidation event. The process can be configured to read signals from the fluorescence-based instrument at a fluorescence wavelength pair of about 230/345 nm±30 nm in excitation and emission as an indicator of microbial activity, or, alternatively at the excitation/emission wavelengths of about 325/470 nm±30 nm in excitation and emission as an indicator of dissolved organic carbon. Beyond the specified tolerances, many other fluorescence wavelength pairs could be useful of this application, and the fluorescence wavelength pair used may be specific to the source water quality and system-specific conditions.

The foregoing has outlined in broad terms some of the more important features of the invention disclosed herein so that the detailed description that follows may be more clearly understood, and so that the contribution of the instant inventors to the art may be better appreciated. The instant invention is not to be limited in its application to the details of the construction and to the arrangements of the components set forth in the following description or illustrated in the drawings. Rather, the invention is capable of other embodiments and of being practiced and carried out in various other ways not specifically enumerated herein. Finally, it should be understood that the phraseology and terminology employed herein are for the purpose of description and should not be regarded as limiting, unless the specification specifically so limits the invention.

BRIEF DESCRIPTION OF THE DRAWINGS

These and further aspects of the invention are described in detail in the following examples and accompanying drawings.

FIG. 5A contains an example illustration of fluorescence EEMs and the scores (in italics) out of a possible 78 days for which each respective signal in Stage 2 was greater than the CAT for (5A) select excitation-emission wavelength pairs noted parenthetically. Note: the superimposed background excitation-emission matrix in 5A is presented for purposes of illustration only.

FIG. 5B contains an example illustration of fluorescence EEMs and the scores (in italics) out of a possible 78 days for which each respective signal in Stage 2 was greater than the CAT for regional areas (R1-R7) determined by summing the fluorescence intensities contained within each area of the EEM. Note: the superimposed background excitation-emission matrix in 5B is presented for purposes of illustration only.

FIG. 6A contains an example annular reactor experiment results showing (6A) influent monochloramine and inorganic nitrogen.

FIG. 6C contains an example annular reactor experiment results showing influent PRI (excitation 230 nm and emission 345 nm) fluorescence.

FIG. 6E contains an example annular reactor experiment results showing influent FDOM (excitation 325 nm and emission 470 nm) fluorescence.

In FIGS. 6A-6F, numbers on each panel (1, 2, and 3) represent nitrification-related Stages 1, 2, and 3, respectively, and are separated by vertical dashed lines. The horizontal dashed lines in FIGS. 6C, 6D, 6E, and 6F are the 99% confidence intervals about the mean fluorescence value in Stage 1, the upper of which is the corrective-action threshold or CAT. The horizontal dashed-dotted lines in FIGS. 6C and 6E are the 99% confidence intervals about the mean of fluorescence in Stages 2 and 3.

DETAILED DESCRIPTION OF THE INVENTION

Figure 1A:
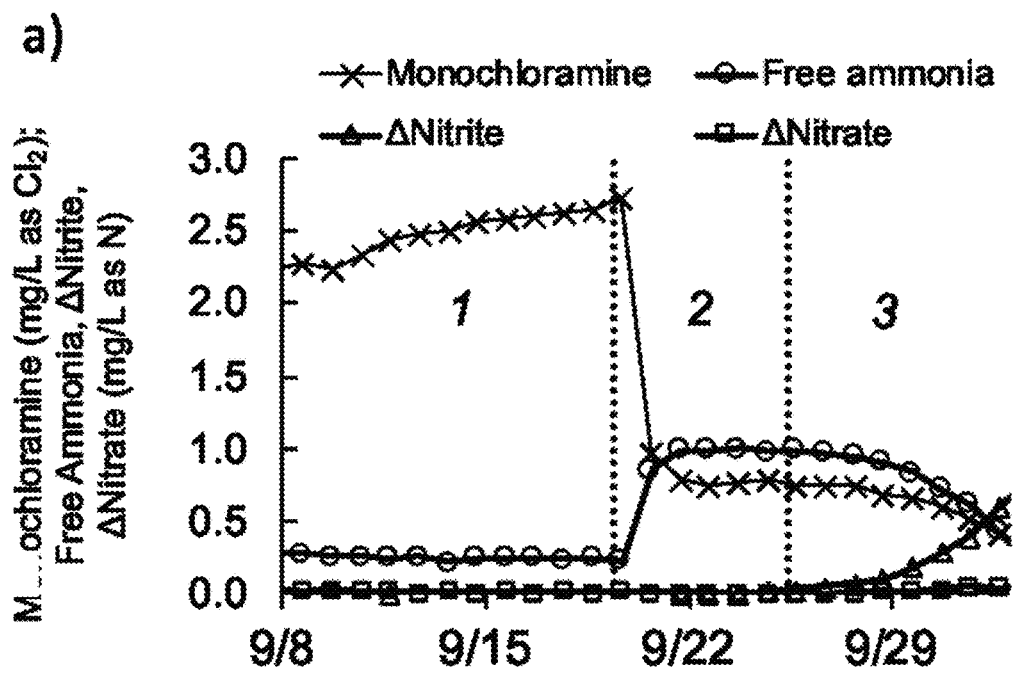
FIG. 1A contains an embodiment of an annular reactor test using water from Drinking Water Utility A. effluent monochloramine, effluent free ammonia, and the production of nitrite (ΔNitrite) and nitrate (ΔNitrate) in the effluent relative to the influent The numbers 1, 2, and 3 represent the Stages of biological ammonia oxidation and are separated by the dotted-vertical lines.

While this invention is susceptible of embodiment in many different forms, there is shown in the drawings, and will herein be described hereinafter in detail, some specific embodiments of the instant invention. It should be understood, however, that the present disclosure is to be considered an exemplification of the principles of the invention and is not intended to limit the invention to the specific embodiments or algorithms so described.

This invention relates generally to a system and process for early detection of biological ammonia oxidation in water utilizing a fluorometry system configured to read increases in a fluorescence excitation-emission wavelength pair that is responsive in a period of time (days to weeks and perhaps even longer) prior to the onset of biological ammonia oxidation, which is considered to be a nitrification event. Note that for purposes of the instant disclosure, the term "nitrification" should be understood to mean the biological process including biological ammonia oxidation and/or biological nitrite oxidation.

Traditionally, such events are confirmed through measurement of inorganic nitrogen, most notably the free ammonia and nitrite concentrations. If free ammonia and nitrite are stable, biological ammonia oxidation is not occurring; however, the fluorescence excitation-emission wavelength pairs including those at an excitation of about 230 nm±30 nm and emission of about 345 nm±30 nm or excitation of about 325 nm±30 nm and emission of about 470 nm+30 nm increase in the time period (days to weeks and perhaps even longer) prior to the onset of ammonia oxidation (i.e., during the period in which the free ammonia and nitrite concentrations are stable), providing an early warning that a biological ammonia oxidation event will subsequently occur unless a remedial action is taken. The system and process enable drinking water utilities to improve management of their distribution systems and facilitate earlier corrective actions, resulting in less or no loss of treated drinking water through flushing (e.g., Given the quantities of water loss due to biological ammonia oxidation (billions of gallons per year for some large utilities), the inventive system and process aids in dramatically decreasing these drinking water losses.

One inventive system and process for early detection of biological ammonia oxidation in water uses a fluorescence-based instrument, electronics and analytical software technology to take fluorescence readings at fluorescence excitation/emission wavelengths of about 230/345 nm±30 nm (and/or about 325/470 nm±30 nm), as well as other wavelength pairs depending on the water quality and source water properties, thereby allowing the water utility to take proactive steps (e.g., optimizing chloramine formation, increasing chloramine concentration, minimizing free ammonia, or reducing system water age) to reduce or prevent the otherwise impending biological ammonia oxidation event. The system and process disclosed herein may include a control system that utilizes a continuous stream methodology or a sample and hold methodology, wherein a side stream is used to sample the water in a main loop and hold for evaluation.

In view of the fact that most drinking water that undergoes biological ammonia oxidation tends to have greater total organic carbon (ca. 1-5 mg·$L^{-1}$ as C), for these waters a fluorescence wavelength pair at approximately 230/345 nm±30 nm in excitation and emission or 325/470 nm±30 nm in excitation and emission may be preferred for early detection of biological ammonia oxidation. The 325/470 nm wavelength pair is particularly well suited for use with waters with at least moderate total organic carbon content (ca. 1 mg·$L^{-1}$ as C or greater). On the other hand, the 230/345 nm combination would be useful for all waters and that combination may be preferable to 325/470 nm for waters with low total organic carbon (e.g., less than ca. 1 mg/L).

An embodiment of a fluorescence-based instrument includes a main processing board and a power supply. The electronics and controls systems can comprise two (2) subsystems: a data acquisition subsystem and a data analysis subsystem. The data acquisition subsystem includes any valves and pumps needed to sample and hold water from the main loop for evaluation. In addition, the data acquisition subsystem provides the drive signal to take readings at the fluorescence excitation wavelength of approximately 230 nm±30 nm and the emission wavelength of approximately 345 nm±30 nm (and/or at 325/470 nm±30 nm in both excitation and emission) as an indicator of microbial activity and/or dissolved organic carbon. The signals from the instrument are then electronically transmitted and processed by the data analysis subsystem to produce a numerical value related to impending biological ammonia oxidation. The system and process disclosed herein may allow for multiple reads, which can be averaged for each respective frequency, thereby eliminating any outliers from the calculations, or differences in frequency response can be used to confirm a given numerical value. Also, any high-frequency variations that may exist due to noise in the system can be eliminated to yield a more accurate result.

By way of example, not limitation, one embodiment of a system suitable for use with the instant invention can also include a plurality of suitable electrical circuitry, including a power supply circuit for the instrument and any required relay controls for external devices, a microcontroller or microprocessor circuit, a serial communication interface circuit, a display circuit, a keypad and configuration switches circuit, and other circuits. The circuits of the instrument are in communication with the microcontroller or microprocessor, and each of the circuits of the instrument includes suitable electrical components.

By way of further example, the instrument of the system and process disclosed herein may use the central microprocessor to control the overall operation of the system and a system bus that connects the central processor to one or more conventional components, such as a network card or modem, via the external communication lines. The instrument may also include a variety of interface units and drives for reading and writing data or files. Depending on the type of device, the user could interact with the system using a keyboard, pointing device, microphone, pen device or other input device. The instrument may be connected to a remote computer via a suitable network connection, such as a phone line, Ti line, a common local area network ("LAN") or other mechanism for connecting computer devices. Data storage electronics, such as serial flash memory, permits storage of audio files, data files, concentration readings and other information. Further, the system may include other suitable interface connectors, such as a multi-pin plug, USB, Bluetooth, etc.

It should be noted and remembered that although real-time measurements would work and would be preferable in many situations, fluorescence measurements taken on samples collected in the field and brought back to the lab for measurement could be useful in many circumstances.

Figure 1B:
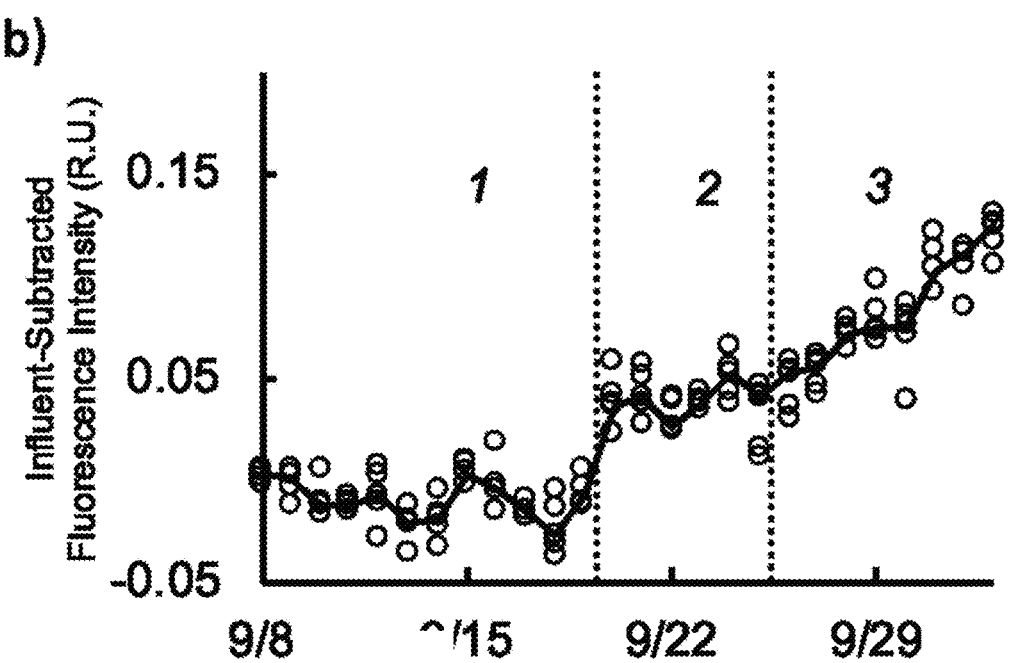
FIG. 1B contains an embodiment of an annular reactor test using water from Drinking Water Utility A. influent-subtracted effluent fluorescence signal at an excitation wavelength of 325 nm and emission wavelength of 470 nm in Raman Units. The numbers 1, 2, and 3 represent the Stages of biological ammonia oxidation and are separated by the dotted-vertical lines.
Figures 2A, 2B:
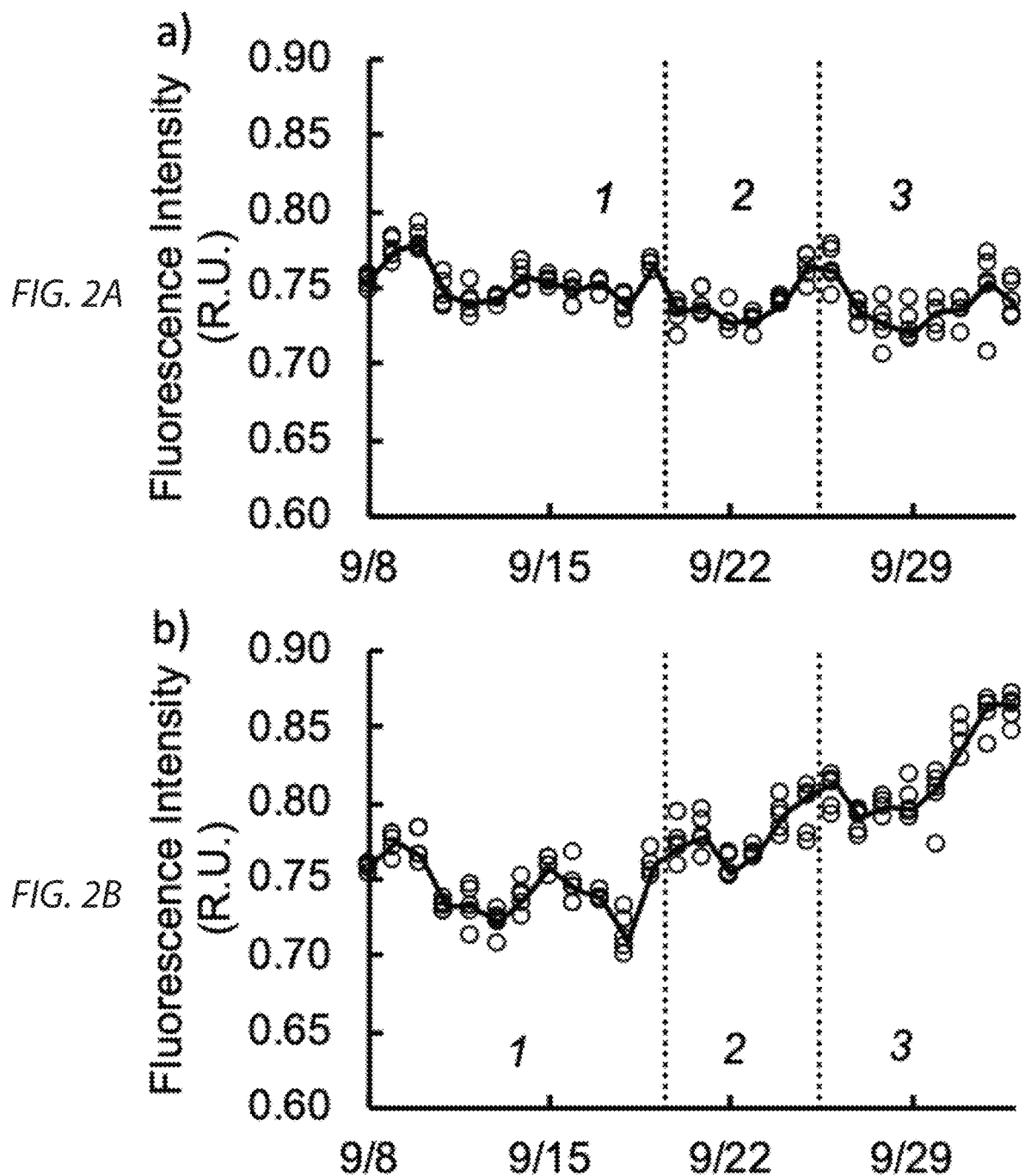
FIG. 2A is an embodiment of an annular reactor fluorescence signal at an excitation wavelength of 325 nm and emission wavelength of 470 nm in Raman Units from the test using water from Drinking Water Utility A shown in FIG. 1. influent of the annular reactor. The numbers 1, 2, and 3 represent the Stages of biological ammonia oxidation (see text) and are separated by the dotted-vertical lines.
FIG. 2B is an embodiment of an annular reactor fluorescence signal at an excitation wavelength of 325 nm and emission wavelength of 470 nm in Raman Units from the test using water from Drinking Water Utility A shown in FIG. 1. effluent of the annular reactor. The numbers 1, 2, and 3 represent the Stages of biological ammonia oxidation (see text) and are separated by the dotted-vertical lines.
Figure 3A:
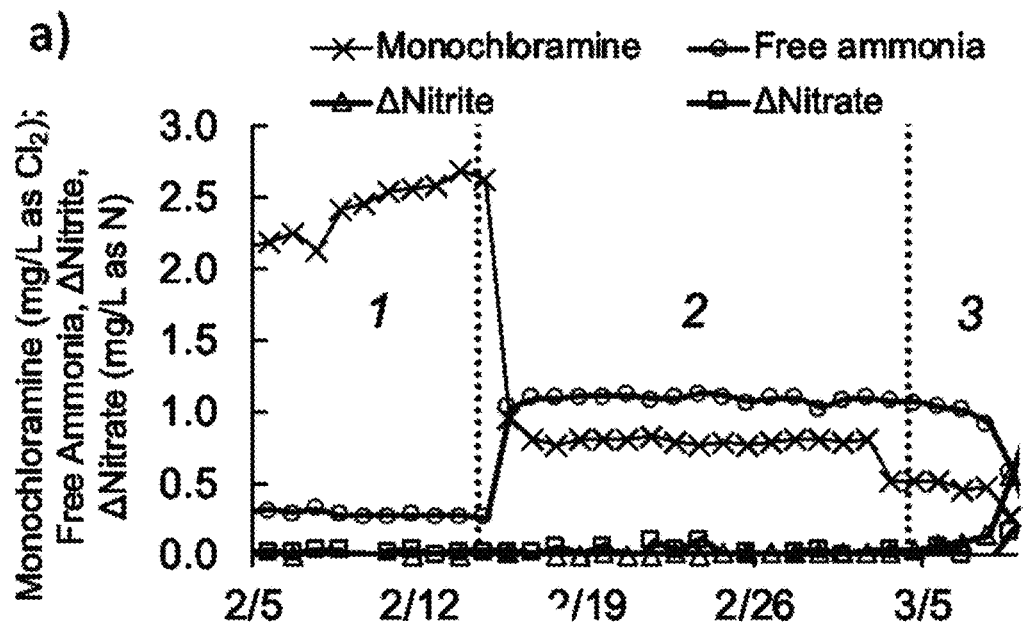
FIG. 3A is an example annular reactor test using water from Drinking Water Utility B. effluent monochloramine, effluent free ammonia, and the production of nitrite (ΔNitrite) and nitrate (ΔNitrate) in the effluent relative to the influent. The numbers 1, 2, and 3 represent the Stages of biological ammonia oxidation (see text) and are separated by the dotted-vertical lines.
Figure 3B:
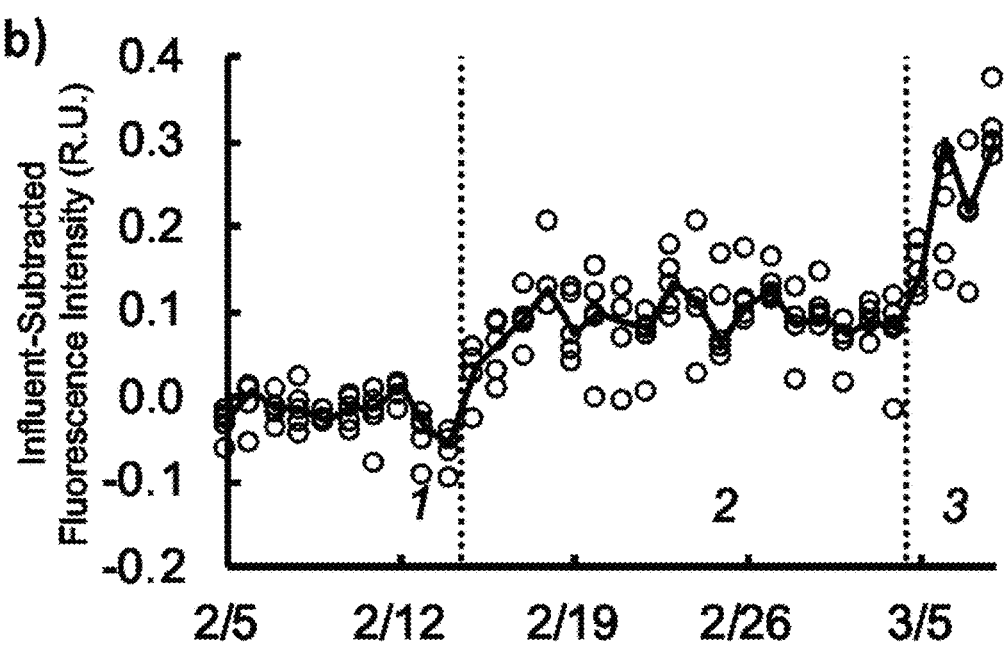
FIG. 3B is an example annular reactor test using water from Drinking Water Utility B. influent-subtracted effluent fluorescence signal at an excitation wavelength of 325 nm and emission wavelength of 470 nm in Raman Units. The numbers 1, 2, and 3 represent the Stages of biological ammonia oxidation (see text) and are separated by the dotted-vertical lines.

Turning next to the figures, as illustrated in FIGS. 1 through 3, one embodiment of the inventive system and process determines the fluorescence excitation-emission wavelength pair that is responsive to the period of time (days to weeks in advance or even longer) prior to the onset of biological ammonia oxidation. The data in FIGS. 1 through 5 were generated in laboratory-scale experiments with daily sampling of the system and using analytical equipment for various measurements, including fluorescence at many wavelength pairs. As shown in FIG. 1A, during Stage 2, free ammonia and monochloramine are stable with no obvious signs of biological ammonia oxidation; however, in FIG. 1B, during Stage 2, a fluorescence wavelength pair—at an excitation of 325 nm and emission of 470 nm—is increasing. Note FIG. 1B was developed by subtracting the data in FIG. 2B (annular reactor effluent fluorescence signal at 325/470 nm) from the daily median values of that in FIG. 2A (annular reactor influent fluorescence signal at 325/470 nm). Biological ammonia oxidation begins in the start of Stage 3 as the free ammonia and monochloramine begin to decrease as shown in FIG. 1A. The fluorescence-based instrument is configured to read the fluorescence signal related to impending biological ammonia oxidation (i.e., FIG. 1B), which is the beginning of the deleterious nitrification process in distribution systems. The inventive system and process allow water utilities to take real-time fluorescence readings at an appropriate wavelength pair, which may be specific to the source water quality and treatment, and based on those readings from the fluorescence-based instrument along with software that facilitates corrections of water quality derived interferences, take remedial action during Stage 2 instead of during Stage 3 when measurable biological ammonia oxidation is occuring. This early remedial action by water utilities would be less drastic and result in less or no loss of treated drinking water in the distribution system due to flushing.

Nine laboratory-scale annular reactor tests were completed using water collected from Drinking Water Utility A (six tests) and Drinking Water Utility B (three tests). The laboratory-scale annular reactor experiments are a scaled-down representation of a length of service pipe in a chloraminated drinking water distribution system. The influent conditions of the annular reactor tests were controlled such that at some time during each experiment, biological ammonia oxidation begins, in which measurable production of nitrite and/or nitrate occurs (greater than 0.05 mg·L$^{-1}$ as N) along with decrease in effluent monochloramine (greater than 0.1 mg·L$^{-1}$ as Cl$_2$). Daily fluorescence measurements of the annular reactor influent and effluent were made in quintuplicate (i.e., five measurements) in addition to daily single measurements of UV spectra, pH, monochloramine, free ammonia, nitrite, and nitrate throughout each experiment. Statistical analyses were completed on the fluorescence data and, by comparison to the monochloramine, nitrite, and nitrate data, the early-warning biological ammonia oxidation fluorescence signal was validated in all nine experiments. For validation, Tukey's tests at the $\alpha=0.01$ significance-level were used to compare the fluorescence signals from the three Stages of the annular reactor tests. Tukey's test is one of any number of statistical tests for determining significant differences in mean values calculated on different groups of observations and those of ordinary skill in the art will recognize that other tests could have been used instead. Additionally, although the testing reported herein was done at an $\alpha=0.01$ significance-level, those of ordinary skill in the art will recognize that the tests could have been done at any arbitrary value of a including, for example, $\alpha=0.05$, $\alpha=0.1$, etc. The same could be said for all of the statistical results reported herein.

In Stage 1 or the period in which the fluorescence baselines were established, there is no measurable production of nitrite and/or nitrate in the effluent relative to the influent. Stated another way, the change in nitrite ($\Delta$Nitrite) and change in nitrate ($\Delta$Nitrate) were less than 0.05 mg·L$^{-1}$ as N. Skipping ahead to Stage 3, there is measurable production of nitrite and/or nitrate, meaning one or both of the $\Delta$Nitrite and $\Delta$Nitrate were greater than 0.05 mg·L$^{-1}$ as N. Therefore, Stage 3 is the start of a biological ammonia oxidation event defined by traditional metrics and can be determined by spatiotemporal measurements of monochloramine, nitrite, and nitrate using various well-established wet chemistry techniques.

It is important to note that the fluorescence-based methods documented in this application utilize the previously unrecognized existence of a period of time—referred to herein as Stage 2—of a biological ammonia oxidation event. The $\Delta$Nitrite and $\Delta$Nitrate are less than 0.05 mg·L$^{-1}$ as N, but the fluorescence signals at 230/345 nm (FIG. 3B) and 325/470 nm (FIG. 1B) and others, are statistically greater during Stage 2 compared to the Stage 1 baseline data acquisition period (e.g., at $\alpha=0.01$). Stage 2 is immediately followed by Stage 3 in which this fluorescence signal is also greater than in the Stage 1 baseline data acquisition period (e.g., $\alpha=0.01$). Thus, the fluorescence signals at 325/470 nm and/or at 230/340 nm, and others, can be used as an early-warning indicator of biological ammonia oxidation.

It should be noted and remembered that the excitation-emission wavelength pairs noted above are not the only pairs that might prove to be useful. Instead, those of ordinary skill in the art will recognize that wavelengths proximate to those values would work as well and wavelengths that are further away might possibly work, depending on the source water quality and treatment processes for a given water utility. For purposes of the instant disclosure, when in each case when an excitation-emission wavelength pair is mentioned it should be understood that there is a range of useful wavelengths that may be employed. With respect to the 230/340 nm pair, excitation wavelengths between about 225 and 250 nm and emission wavelengths between about 320 and 380 nm have proven to be reliable early warning indicators of biological ammonia oxidation (e.g., Region R2 of FIG. 5B). FIG. 5 is discussed at some length below. Similarly, with respect to the 325/470 nm pair, excitation wavelengths between about 300 nm and 400 nm and emission wavelengths between about 380 nm to 600 nm have also proven to be reliable early warning indicators of biological ammonia oxidation under the circumstances described previously (i.e., Region R7 of FIG. 5B). See also, Table 1 for more details with respect to the most reliable excitation-emissions wavelength pairs for early warning detection of biological ammonia oxidation in the annular reactor tests with source waters from Drinking Water Utility A and B. Please note however, these results may change for source waters from other water utilities and operational conditions dissimilar to those used here (see FIG. 1A and FIG. 3A).

FIG. 1 shows an example data set collected from one of six annular reactor experiments with water from Drinking Water Utility A. FIG. 1A shows the effluent monochloramine, effluent ammonia, and the production of nitrite and nitrate in effluent relative to the influent (i.e., $\Delta$Nitrite and $\Delta$Nitrate). FIG. 1B shows the fluorescence signal at 325/470 nm in the effluent relative to the influent, denoted as the Influent-subtracted Fluorescence Intensity and presented in Raman Units (R.U.), a standard unit for fluorescence data. FIG. 1A shows in Stage 2, there is no measurable production of nitrite or nitrate. Thus, using these traditional biological ammonia oxidation-related metrics, biological ammonia oxidation has not been detected. However, the fluorescence signal (see FIG. 1B) is greater in each day of Stage 2 compared to the Stage 1 baseline data ($\alpha=0.01$). Biological ammonia oxidation, as defined by measurable nitrite or nitrate production (greater than 0.05 mg·L$^{-1}$ as N) begins at the start of Stage 3 and continues throughout the duration of Stage 3 (see FIG. 1A). In Stage 3, the fluorescence signal continues to increase and is greater than that in Stage 1 ($\alpha=0.01$). The statistically-significant increase in the fluorescence signal in Stage 2 relative to the Stage 1 baseline indicates that the fluorescence signal can be used as an early-warning indicator of biological ammonia oxidation. As shown in FIG. 1B, this signal provides six days of early-warning compared to traditional methods used to detect biological ammonia oxidation.

FIG. 2 demonstrates that the signal shown in FIG. 1B is not due to the change in monochloramine from Stages 1 to 2 (see FIG. 1A) that was purposefully made to induce biological ammonia oxidation. Tukey's test was used to compare the influent fluorescence signal from the last day of Stage 1 to the first day of Stage 2 (FIG. 2A). This comparison showed that the fluorescence signal in the influent decreased ($\alpha=0.01$) from the last day of Stage 1 to the first day of Stage 2. FIG. 2B shows, however, there was a statistically-significant increase in 325/470 nm in the effluent on the first day of Stage 2. This increase is also observed in the influent-subtracted effluent fluorescence signal (FIG. 2B), demonstrating the increase in 325/470 was not due to changes in the influent signal.

Similar results are shown in FIGS. 3 and 4 from an annular reactor experiment with water from Drinking Water Utility B. FIG. 3 shows that Stage 2 was 18 days in duration and the fluorescence signal at 325/470 nm was greater in each of the 18 days relative to that in Stage 1 ($\alpha=0.01$). Therefore, in this example the 325/470 fluorescence signal provides eighteen days of early-warning compared to traditional methods used to detect biological ammonia oxidation which include the measurement of nitrite and monochloramine.

Figure 4A:
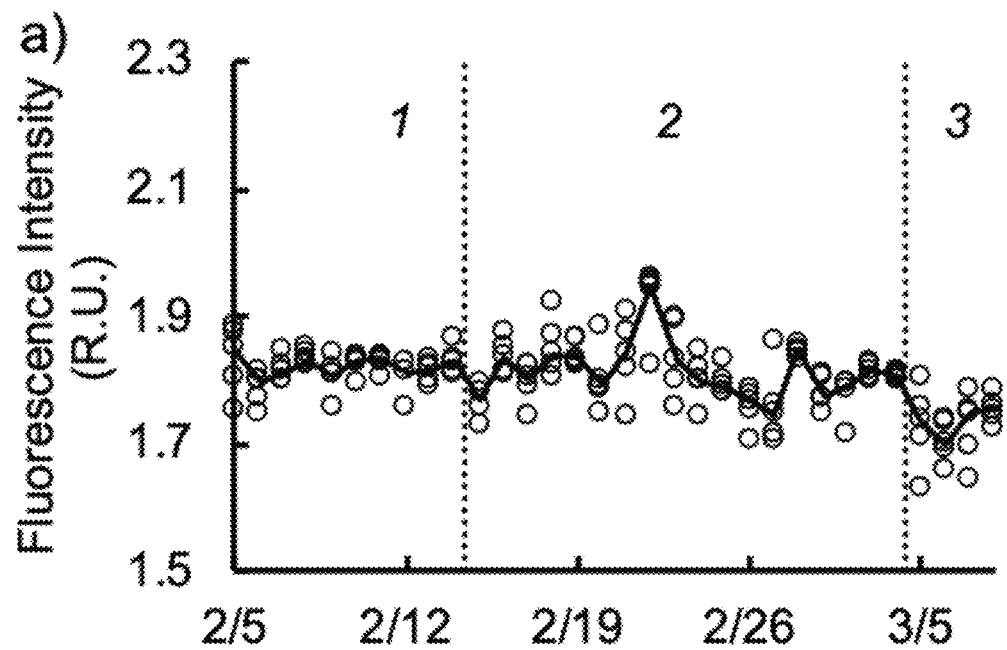
FIG. 4A contains an example of an annular reactor fluorescence signal at an excitation wavelength of 325 nm and emission wavelength of 470 nm in Raman Units from the annular reactor test using water from Drinking Water Utility B shown in FIG. 3. influent of the annular reactor. The numbers 1, 2, and 3 represent the Stages of biological ammonia oxidation and are separated by the dotted-vertical lines.
Figure 4B:
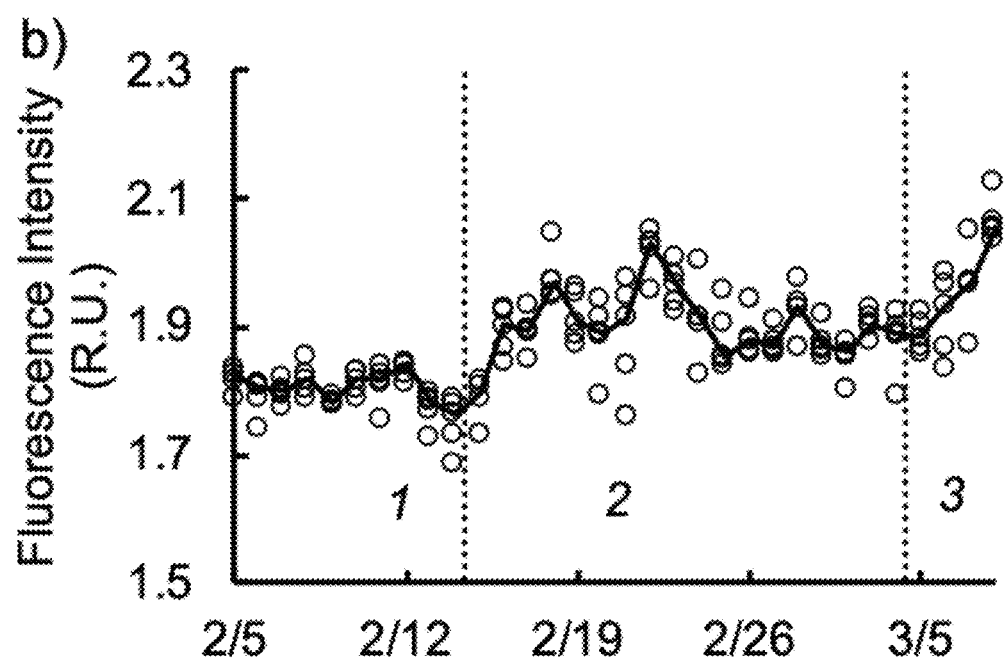
FIG. 4B contains an example of an annular reactor fluorescence signal at an excitation wavelength of 325 nm and emission wavelength of 470 nm in Raman Units from the annular reactor test using water from Drinking Water Utility B shown in FIG. 3. effluent of the annular reactor. The numbers 1, 2, and 3 represent the Stages of biological ammonia oxidation and are separated by the dotted-vertical lines.

FIG. 4A demonstrates there was a statistically-significant decrease ($\alpha=0.01$) in the influent fluorescence signal from the last day of Stage 1 compared to the first day of Stage 2 and FIG. 4B demonstrates there was a statistically-significant increase ($\alpha=0.01$) as compared with the baseline during Stage 2. Thus, the increase observed in FIG. 3 at the start of Stage 2 was not caused by an increase in the influent fluorescence signal but rather an early warning indicator of impending biological ammonia oxidation.

All nine annular reactor tests show results similar to those in FIGS. 1-4. There was a statistically-significant increase ($\alpha=0.01$) in the influent-subtracted effluent fluorescence signal at 230/345 nm and 325/470 nm in Stage 2 relative to that in Stage 1. Similarly, there was a statistically significant ($\alpha=0.01$) increase in 230/345 nm and 325/470 nm in Stage 3 relative to Stage 1. It can be concluded that the increase in fluorescence at these wavelength pairs and others precede changes in traditional measures used to detect biological ammonia oxidation such as nitrite and monochloramine can be used reliably as an early-warning indicator for biological ammonia oxidation.

In practice, various embodiments could be implemented as follows. In the most general sense, fluorescence measurements will be used to indicate microbial activity in drinking water. In one embodiment, fluorescence measurements will be used in chloraminated drinking water distribution systems as (1) an early warning indicator of microbial activity (e.g., ammonia oxidation) and (2) an indicator of the effectiveness of corrective action(s) used to control microbial activity.

Fluorescence measurements could be collected at one or more locations in the drinking water distribution system, either manually or automatically/continuously, where "continuously" should be understood to mean that measurements are repeatedly collected at some predetermined time interval or intervals, for example, every hour, three times a day, several times a day, every day, weekly, etc. The sample interval is a parameter that can readily be determined by one of ordinary skill in the art who is familiar with the generally characteristics of the distribution system. Preferably, the sample interval will be kept relatively constant, but that is not a requirement.

In the instance where measurements are collected at one location in the distribution system, a baseline fluorescence will preferably be established that corresponds to the characteristics of the water in that distribution system at that point during a period of low microbial activity or, perhaps, after the system has been flushed or after chemical remedial action has been taken. For purposes of the instant disclosure, the term "remediation effort" will refer to chemical or physical (e.g., flushing) all or part of the distribution system after Stage 2 has been detected.

The duration of the baseline development period will likely range from several days to a few weeks and depend on the number of fluorescence measurements taken each day (which might be selected by the water utility) and system operational characteristics. If the measurements are collected at multiple locations, they could be combined (e.g., using a mean, median, etc.) into a single value or each location could be treated separately according to the example that follows.

Continuing with the present embodiment, a corrective action threshold (CAT) will be calculated which is based on the baseline measurements. Subsequently measured values that exceed this level will be an indication that the water system is entering Stage 2, i.e., that biological ammonia oxidation will become problematic in the subsequent days to weeks. If multiple locations have been tested, it may be that one location has crossed the CAT ahead of the others which might provide important information to the individual(s) tasked with maintaining water quality.

As one example of how the CAT level might be set would be to determine confidence intervals about the mean of the fluorescence baseline data as is illustrated in Stage 1 of the annular reactor tests. The confidence intervals could be selected according to some predetermined probability level, preferably the 99% level so as to minimize instances of false-positive signals, although other probability levels (e.g., 90%, 95%, etc.) could be used. An example of how this computation might be used in practice is illustrated in Stage 1 of the annular reactor tests shown in FIGS. 6D and 6F. Influent-subtracted-effluent fluorescence measurements above the CAT are early warning indicators for nitrification.

In distribution system measurements, in some embodiments fluorescence measurements will be compared to the CAT, and if measured data exceeds the CAT for more than a utility-set number of measurements in a period of time (e.g., three measurements in 24 hours), this will be considered an early warning signal for nitrification. This scenario may require recalculation of baselines on a seasonal basis and in response to changes in source water quality (e.g., changes in organic matter or supplementing surface water with ground water), changes in disinfectant type (e.g., free chlorine or chloramines), or modifications to treatment processes in the water treatment plant.

For utilities that collect fluorescence measurements at multiple locations in the distribution system, fluorescence measurements taken in areas of the distribution system with low water age and low microbial activity (e.g., entry points to the distribution system) will be used to adjust baselines at downstream sites. In addition, comparison of fluorescence measurements collected at upstream and downstream monitoring locations will be used to map areas of the distribution system impacted by microbial activity to facilitate targeted maintenance.

Those of ordinary skill in the art will recognize that the example method of determining when a water distribution system enters Stage 2 is just one of many such approaches to detecting changes in an underlying time series. Additionally, in some embodiments it might be useful to filter the data series (e.g., a low pass filter) to reduce the effect of random noise or measurement error. Further, some tests might be based on a departure from stationarity of the baseline data.

Those of ordinary skill in the art will be capable of devising an appropriate statistical or deterministic test to recognize the onset of Stage 2.

After an early warning signal is detected and a corrective action is taken by the water utility, fluorescence measurements could be used to evaluate the effectiveness of the response for halting the processes that led to microbial activity. For example, in chloraminated drinking water systems, conversion to free chlorine from chloramines as the disinfectant is one such response to control microbial activity (i.e., nitrification). In addition, a yearly free chlorine conversion for approximately one month is required in some states (e.g., North Carolina) for chloramine systems. Currently, the time period of the free chlorine conversion and its effectiveness are evaluated based on chemical measurements conducted on the bulk water within a drinking water system. However, basing process control on bulk water chemical measurements overestimates the effectiveness of the control measure on microbial activity, leading to insufficient time periods of corrective actions as evidenced by recurring nitrification episodes in chloramine systems once regular operation resumes. Using fluorescence measurements to establish when the system baseline has returned to within the CAT would allow for a quantitatively-based assessment of required time period for free chlorine conversion or other corrective actions to ensure inactivation of nitrifying bacteria attached to interior pipe surfaces and/or sediments.

It is also possible that fluorescence measurements could be used to identify undesirable flow patterns within the distribution system due to unintentionally closed or opened valves. Fluorescence measurements may also be useful in understanding the extents of blending zones within distribution systems and to evaluate water age within distribution systems, including storage tank turnover.

Returning to the current example when a drinking water utility exceeds a determined CAT, an operational and/or maintenance response will be typically initiated. Many utilities that use chloramines maintain nitrification action plans, which list concentrations of traditional chemical monitoring parameters (e.g., total chlorine, monochloramine, free ammonia, nitrite, nitrate) associated with normal operating conditions and possible nitrification events. These plans also document actions that the utility will take in response to detection of a possible nitrification event. Common responses to nitrification events are detailed in the American Water Works Association M56 manual of practice.

Fluorescence measurements of the sort described herein could be incorporated into nitrification action plans and changing fluorescence measurements would trigger responses earlier than traditional chemical monitoring parameters. The nature of the response will vary based on the location where the early warning signal is detected and possibly the magnitude of the CAT exceedance. Initial chemical responses could include (1) increasing disinfectant (e.g., chlorine or chloramine) doses at the water treatment plants or upstream booster disinfectant locations in the distribution system to increase disinfectant residual and/or (2) decreasing free ammonia residuals to inhibit microbial activity. For areas of the distribution system where water storage tanks impact water quality, the response could include, by way of example only, increasing tank turnover to decrease water age, thereby increasing monochloramine residuals in the system or, in the alternative, taking tanks out of service. Some locations, such as dead ends or areas with low water usage, will be flushed to bring fresh water with higher monochloramine residuals into the area.

The early warning signal provided by fluorescence measurements will help operators respond to microbial activity before the disinfectant residual in the system is lost or before microbial activity (e.g., nitrification) has spread to large areas of the distribution system. The fluorescence measurements will also signal to operators when a given remedial action has been successful. For example, if operators increase the disinfectant residual, the fluorescence measurements will continue to indicate impending microbial activity (i.e., exceedances of the CAT) until the disinfectant residual is sufficient to inhibit microbial activity. This will result in improved water quality in the distribution system and reductions in the amount of water needed to flush the distribution system.

Although two excitation/emission wavelengths have proven to be very useful (e.g., 230/345 nm and 325/470 nm), those of ordinary skill in the art will recognize that there is a broad range of excitation/emission wavelengths that could be useful, and could depend on the source water characteristics in the distribution system. The physically-possible combinations of the excitation-emission spectra result in an excitation-emission matrix or EEM as is generally indicated in the example of FIG. 5.

FIG. 5 is a representation of test results in which the excitation spectrum spanned 225-400 nm with 1 nm step sizes and the emission spectrum spanned 270-600 nm with 5 nm step sizes. Following removal of first- and second-order Raman and Rayleigh scattering peaks (white regions in FIG. 1), a total of 7,797 fluorescence intensities were collected for each EEM. These are typical spectral ranges, step sizes, and data processing techniques used in fluorometry, but these can vary by instrument type and lab.

Figure 6B:
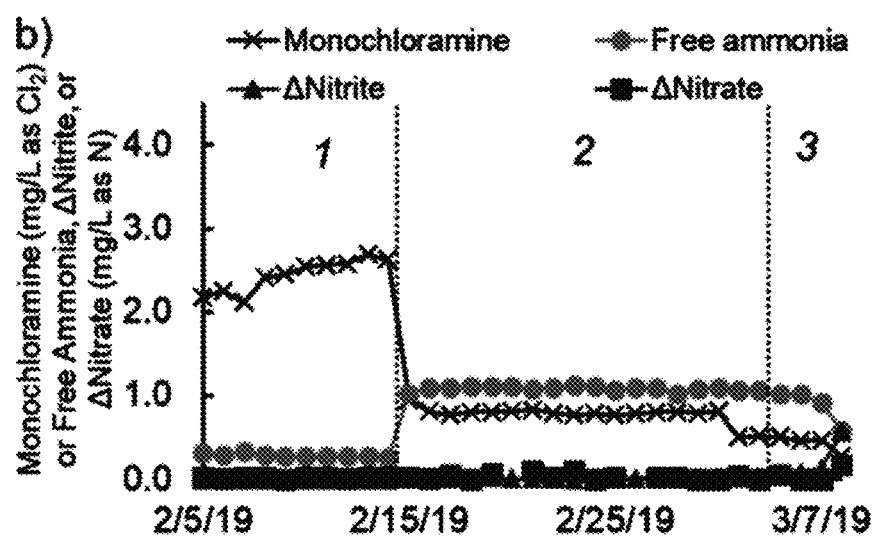
FIG. 6B contains an example annular reactor experiment results showing effluent monochloramine and inorganic nitrogen.
Figure 6D:
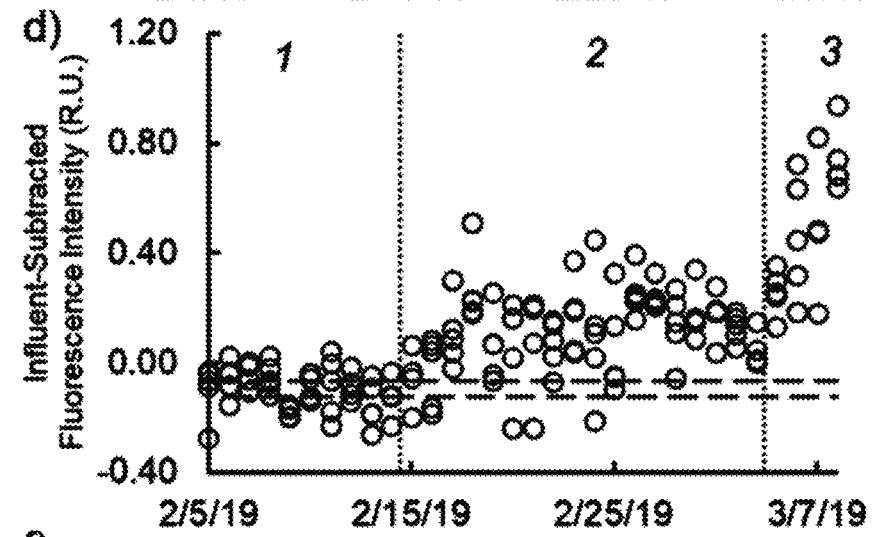
FIG. 6D contains an example annular reactor experiment results showing influent-subtracted effluent PRI fluorescence.
Figure 6F:
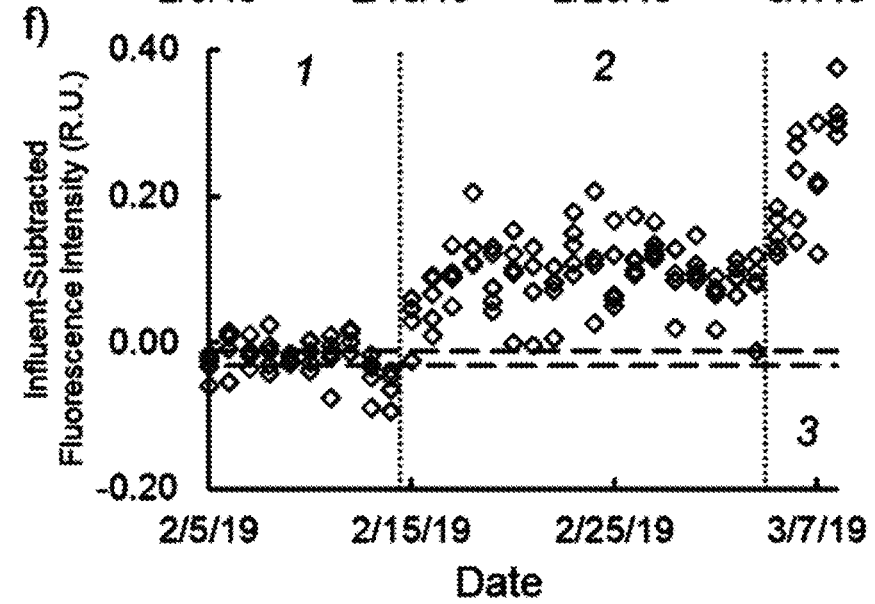
FIG. 6F contains an example annular reactor experiment results showing influent-subtracted effluent FDOM fluorescence.

A total of nine annular reactor tests were completed and, on each day, five EEMs were collected on the influent and another five on the effluent. To account for variability in the influent fluorescence, each of the daily effluent EEMs (n=5) were transformed by subtracting the corresponding influent median (n=5) for each of the 7,797 fluorescence intensities. This transformation is intended to highlight fluorescence fluorophores that were formed in the annular reactor. The resulting plots from one annular reactor experiment are shown in FIG. 6, where the left-side panels show the influent conditions, with monochloramine, free ammonia, nitrite, and nitrate in FIG. 6A, the fluorescence signal at excitation of 230 nm and emission of 345 nm (referred to as PRI) in FIG. 6C, and the fluorescence signal at excitation of 325 nm and emission of 470 nm (referred to as FDOM) in FIG. 6E. The corresponding effluent profiles are shown in the right-side panels with the PRI (FIG. 6D) and FDOM (FIG. 6F) signals presented as influent-median-subtracted effluent signals. Statistical analyses were performed on the resultant influent-median-subtracted effluent signals to assess their suitability as an early-warning indicator of microbial activity, specifically, biological ammonia oxidation. For each influent-subtracted-effluent signal, the upper and lower 99% confidence intervals (i.e., CAT) were calculated about the mean of the fluorescence data collected during Stage 1. During Stages 2 and 3, days when all five influent-subtracted-effluent points were above the CAT were taken as early-warning indictors (Stage 2) or on-going indicators (Stage 3) of biological ammonia oxidation. FIG. 6F shows the FDOM signal exceeds the CAT in 88 out of 90 measurements Stage 2 (98%), indicating FDOM was a strong early warning indicator of biological ammonia oxidation, which can be measured using traditional chemical parameters at the start of Stage 3. FIG. 6D shows the PRI signal exceeds the CAT in 78 out of 90 measurements Stage 2 (87%), indicating PRI was also good early warning indicator.

To aggregate these results as a function of excitation and emission spectral wavelength, the EEM was divided into seven regions (see FIG. 5B) and the fluorescence intensities from each region were summed. In the nine annular reactor tests, there was a total of 78 days in Stage 2. For each of the seven regions, the number of days in Stage 2 was calculated for which all five influent-median-subtracted effluent signals were greater than the CAT (i.e., upper 99% confidence interval of the mean in Stage 1). Table 1 delineates the seven regions and their respective scores and rankings as an early-warning indicator of biological ammonia oxidation.

TABLE 1

Number of Days in Stage 2 in which the minimum influent-median-subtracted effluent fluorescence measurement (n = 5) was greater than the CAT (upper 99% confidence interval on the mean in Stage 1) for seven regions of the excitation-emission matrix (see FIG. 5B).

| Region | Excitation Range (nm) | | Emission Range (nm) | | Days | % of Days out of a total 78 days | Rank |
| --- | --- | --- | --- | --- | --- | --- | --- |
| | Lower | Upper | Lower | Upper | | | |
| 1 | 225 | 250 | 270 | 330 | 38 | 49 | Poor |
| 2 | 225 | 250 | 330 | 380 | 46 | 59 | Fair |
| 3 | 225 | 250 | 380 | 600 | 61 | 78 | Very Good |
| 4 | 250 | 400 | 270 | 330 | 42 | 54 | Fair |
| 5 | 250 | 400 | 330 | 380 | 51 | 65 | Good |
| 6 | 250 | 300 | 380 | 600 | 64 | 82 | Excellent |
| 7 | 300 | 400 | 380 | 600 | 66 | 85 | Excellent |

The rankings in Table 1 were made based on the percentage of days in Stage 2 in which the minimum influent-median-subtracted effluent fluorescence measurement (n=5) was greater than the upper 99% confidence interval on the mean in Stage 1, as follows: less than 50% was poor, 51-60% was fair, 61-70% was good, 71-80% was very good, and greater than 81% was excellent. Based on these criteria, Region 1 was poor, Regions 2 and 4 were fair, Region 5 was good, Region 3 was very good, and Regions 6 and 7 were excellent. Region 7 was the strongest early-warning indicator at 85% and contains the FDOM signal which has an excitation wavelength of 325 nm and emission wavelength of 470 nm (see FIG. 6A). Of all wavelength pairs, FDOM had the highest score with 87% or 68 out of 78 days in which the signal in Stage 2 exceeded the CAT.

The data in Table 1 indicate that many fluorescence wavelength pairs could be suitable choices for early detection of microbial activity (i.e., biological ammonia oxidation). However, the choice of wavelength pair is important, and in the experiments with waters from Utilities A and B those particularly with emission wavelengths above 380 nm being very good to excellent early warning indicators of biological ammonia oxidation. However, the summary rankings shown in Table 1 could change in the cases of other source waters with different water quality characteristics. However, fluorescence is expected to be similarly reliable as an early warning indicator of biological ammonia oxidation.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional elements.

It is to be understood that where the claims or specification refer to "a" or "an" element, such reference is not be construed that there is only one of those elements.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Systems and processes of the instant disclosure may be implemented by performing or completing manually, automatically, or a combination thereof, selected steps or tasks.

The term "process" may refer to manners, means, techniques and procedures for accomplishing a given task including, but not limited to, those manners, means, techniques and procedures either known to, or readily developed from known manners, means, techniques and procedures by practitioners of the art to which the invention belongs.

For purposes of the instant disclosure, the term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. Terms of approximation (e.g., "about", "substantially", "approximately", etc.) should be interpreted according to their ordinary and customary meanings as used in the associated art unless indicated otherwise. Absent a specific definition and absent ordinary and customary usage in the associated art, such terms should be interpreted to be ±10% of the base value.

When, in this document, a range is given as "(a first number) to (a second number)" or "(a first number)-(a second number)", this means a range whose lower limit is the first number and whose upper limit is the second number. For example, 25 to 100 should be interpreted to mean a range whose lower limit is 25 and whose upper limit is 100. Additionally, it should be noted that where a range is given, every possible subrange or interval within that range is also specifically intended unless the context indicates to the contrary. For example, if the specification indicates a range of 25 to 100 such range is also intended to include subranges such as 26-100, 27-100, etc., 25-99, 25-98, etc., as well as any other possible combination of lower and upper values within the stated range, e.g., 33-47, 60-97, 41-45, 28-96, etc. Note that integer range values have been used in this paragraph for purposes of illustration only and decimal and fractional values (e.g., 46.7-91.3) should also be understood to be intended as possible subrange endpoints unless specifically excluded.

It should be noted that where reference is made herein to a process comprising two or more defined steps, the defined steps can be carried out in any order or simultaneously (except where context excludes that possibility), and the process can also include one or more other steps which are carried out before any of the defined steps, between two of the defined steps, or after all of the defined steps (except where context excludes that possibility).

Still further, additional aspects of the instant invention may be found in one or more appendices attached hereto and/or filed herewith, the disclosures of which are incorporated herein by reference as if fully set out at this point.

Thus, the invention is well adapted to carry out the objects and attain the ends and advantages mentioned above as well as those inherent therein. While the inventive concept has been described and illustrated herein by reference to certain illustrative embodiments in relation to the drawings attached thereto, various changes and further modifications, apart from those shown or suggested herein, may be made therein by those of ordinary skill in the art, without departing from the spirit of the inventive concept the scope of which is to be determined by the following claims.

What is claimed is:

1. A method of treating a body of water in a water distribution system, comprising the steps of:
   a) selecting a fluorescence excitation wavelength and a fluorescence emission wavelength different from said fluorescence excitation wavelength, wherein the fluorescence excitation and emission wavelengths are responsive to components in the body of water in a period of time before an onset of measurable ammonia oxidation in the body of water;
   b) determining a value representative of a baseline amount of fluorescence signal for the body of water excited at the selected fluorescence excitation wavelength and measured at the fluorescence emission wavelength;
   c) selecting a corrective action threshold based on said determined value representative of the baseline amount of fluorescence signal, wherein the corrective action threshold is a threshold amount of the baseline fluorescence signal which represents an acceptable level of ammonia oxidation in the body of water and anything above said threshold amount represents a possible level of ammonia oxidation to occur in the body of water that requires a corrective remedial action in order to prevent further degradation of water quality;
   d) collecting a sample of water from the body of water;
   e) exciting the sample of water at the selected excitation wavelength;
   f) measuring a value representative of an amount of fluorescence signal from the excited sample of water at the selected fluorescence emission wavelength;
   g) comparing said value representative of said measured amount of fluorescence signal with said value representative of the baseline amount of fluorescence signal;
   h) determining that the body of water is in a stage 2 immediately before ammonia oxidation in the body of water begins to occur when the value of the measured amount of fluorescence signal is greater than the corrective action threshold;
   i) initiating a remediation effort when the body of water has entered stage 2 in order to prevent ammonia oxidation from occurring in the body of water; and
   j) when the value representative of the measured amount of fluorescence signal is not greater than the corrective action threshold, determining that the body of water has not entered stage 2 and repeating the steps of the method until it is determined that the body of water has entered stage 2 and requires a remediation effort.

2. A method according to claim 1, wherein said fluorescence excitation wavelength is between 225 nm and 250 nm and said fluorescence emission wavelength is between 330 nm and 380 nm.

3. A method according to claim 1, wherein said fluorescence excitation wavelength is between 300 nm and 400 nm and said fluorescence emission wavelength is between 380 nm and 600 nm.

4. A method according to claim 1, wherein said fluorescence excitation wavelength is 230 nm and said fluorescence emission wavelength is 345 nm.

5. A method according to claim 1, wherein said fluorescence excitation wavelength is 325 nm and said fluorescence emission wavelength is 470 nm.

6. A method according to claim 1, step a) comprises the steps of:
   a1) determining a dissolved organic carbon in the body of water;
   a2) if the dissolved organic carbon is greater than about 1-5 milligram per liter as carbon, selecting a fluorescence excitation wavelength of 230 nm and a fluorescence emission wavelength of 345 nm.

7. A method according to claim 1, wherein said fluorescence excitation wavelength is between 225 nm and 250 nm and said fluorescence emission wavelength is between 270 nm and 330 nm.

8. A method according to claim 1, wherein said fluorescence excitation wavelength is between 225 nm and 250 nm and said fluorescence emission wavelength is between 380 nm and 600 nm.

9. A method according to claim 1, wherein said fluorescence excitation wavelength is between 250 nm and 400 nm and said fluorescence emission wavelength is between 270 nm and 330 nm.

10. A method according to claim 1, wherein said fluorescence excitation wavelength is between 250 nm and 400 nm and said fluorescence emission wavelength is between 330 nm and 380 nm.

11. A method according to claim 1, wherein said fluorescence excitation wavelength is between 250 nm and 300 nm and said fluorescence emission wavelength is between 380 nm and 600 nm.

12. A method according to claim 1, wherein said fluorescence excitation wavelength is between 225 nm and 400 nm and said fluorescence emission wavelength is between one of about 270 nm and 330 nm, about 330 nm and 380 nm, or about 380 nm and 600 nm.

13. A method of determining whether a body of water requires remedial action to prevent biological ammonia oxidation, said method comprising the steps of:
   a) selecting a fluorescence excitation-emission wavelength pair having a signal that changes relative to a baseline fluorescence signal established over a period of time preceding biological ammonia oxidation in the body of water;

b) determining a value representative of the baseline fluorescence signal for the selected fluorescence excitation-emission wavelength pair for the body of water, wherein the value represents the baseline fluorescence signal or a derived value thereof during a period of time during which an acceptable amount of ammonia oxidation has occurred in the body of water;

c) selecting a value representative of a corrective action threshold fluorescence signal relative to a threshold amount of the baseline fluorescence signal, wherein the corrective action threshold fluorescence signal represents an acceptable level of ammonia oxidation in the body of water;

d) collecting a sample of water from the body of water;

e) exciting the sample of water at the selected fluorescence excitation wavelength;

f) measuring a value representative of an amount of fluorescence signal from the excited sample of water at the selected fluorescence emission wavelength;

g) comparing said value representative of said measured amount of fluorescence signal with said value representative of the baseline amount of fluorescence signal;

h) if said value representative of said measured amount of fluorescence signal is greater than said value representative of said corrective action threshold fluorescence signal, determining that the body of water requires a remedial action to prevent or decrease the amount of ammonia oxidation;

i) if said value representative of said measured amount of fluorescence signal is equal to or less than said value representative of said corrective action threshold fluorescence signal, determining that the body of water does not require a remedial action and repeating at least steps (c) through (g) until said value representative of said corrective action threshold fluorescence signal is exceeded; and j) if said value representative of said measured fluorescence signal has exceeded said value representative of the corrective action threshold fluorescence signal, initiating a remedial action until the value representative of the measured fluorescence signal is less than said value representative of the corrective action threshold fluorescence signal.

14. The method of claim 13 wherein the remedial action comprises a chemical treatment of the body of water, a physical treatment of the body of water, or a combination of both chemical and physical treatments of the body of water.

15. The method of claim 13 wherein said fluorescence excitation wavelength is between 225 nm and 250 nm and said fluorescence emission wavelength is between 330 nm and 380 nm.

16. The method of claim 13 wherein said fluorescence excitation wavelength is between 300 nm and 400 nm and said fluorescence emission wavelength is between 380 nm and 600 nm.

17. The method of claim 13 wherein said fluorescence excitation wavelength is 230 nm and said fluorescence emission wavelength is 345 nm.

18. The method of claim 13 wherein said fluorescence excitation wavelength is 325 nm and said fluorescence emission wavelength is 470 nm.

19. The method of claim 13 wherein step a) further comprises the steps of:

a1) determining a dissolved organic carbon in the body of water;

a2) if the dissolved organic carbon is greater than about 1 milligram per liter as carbon, selecting a fluorescence excitation wavelength of 230 nm and an emission and a fluorescence emission wavelength of 345 nm.

20. The method of claim 13 wherein said fluorescence excitation wavelength is between 225 nm and 250 nm and said fluorescence emission wavelength is between 270 nm and 330 nm.

21. The method of claim 13 wherein said fluorescence excitation wavelength is between 225 nm and 250 nm and said fluorescence emission wavelength is between 380 nm and 600 nm.

22. The method of claim 13 wherein said fluorescence excitation wavelength is between 250 nm and 400 nm and said fluorescence emission wavelength is between 270 nm and 330 nm.

23. The method of claim 13 wherein said fluorescence excitation wavelength is between 250 nm and 400 nm and said fluorescence emission wavelength is between 330 nm and 380 nm.

24. The method of claim 13 wherein said fluorescence excitation wavelength is between 250 nm and 300 nm and said fluorescence emission wavelength is between 380 nm and 600 nm.

25. The method according to claim 13 wherein said fluorescence excitation wavelength is between 225 nm and 400 nm and said fluorescence emission wavelength is between one of about 270 nm and 330 nm, about 330 nm and 380 nm, or about 380 nm and 600 nm.

* * * * *